United States Patent [19]

Zwickl

[11] Patent Number: 5,702,937

[45] Date of Patent: Dec. 30, 1997

[54] METHOD FOR POTENTIATING TISSUE PLASMINOGEN ACTIVATOR WITH β-LACTOGLOBULIN

[75] Inventor: Craig M. Zwickl, Indianapolis, Ind.

[73] Assignee: Eli Lilly and Company, Indianapolis, Ind.

[21] Appl. No.: 448,011

[22] Filed: May 23, 1995

[51] Int. Cl.$^6$ .............................. C12N 9/48; C12N 9/00
[52] U.S. Cl. ........................................ 435/212; 435/183
[58] Field of Search ............................... 435/212, 183

[56] References Cited

PUBLICATIONS

Burck et al. (1990) Journal Biol. Chem., 265(9), "Characterization of a Modified human Tissue Plasminogen Activator Comprising a Kringle–2 and a Protease Domain", pp. 5170–5177.

Buessecker, et al., 1993, Enzyme–linked immunosorbent assays for plasminogen activators; *Journal of Immunological Methods* 162: 193–200.

Verheijen, et. al., 1982, Activation of Plasminogen by Tissue Activator is Increased Specifically In The Presence Of Certain Soluble Fibrin(ogen) Fragments; *Thrombosis Research* 27: 377–385.

Ranby, et. al., 1982, A Sensitive Assay For Tissue Plasminogen Activator; *Thrombosis Research* 27: 743–749.

Gyzander, et al., A Sensitive Assay For Tissue Plasminogen Activator Activity In Plasma, Using Adsorption On Lysine–Sepharose, *Thrombosis Research* 35: 547–558, 1984.

Band, et. al., Thrombolytic Therapy In Acute Myocrdial Infarction; *Annu. Rev. Pharmacol. Toxicol*, 1989, 29:323–41.

Takada, et al., The Physiology of the Fibrinolytic System; *Japanese Journal of Physiology* 43: 1–19.

Grines, Thrombolytic, Antiplatelet, and Antithrombotic Agents; *The American Journal of Cardiology*, 1982, 70:18–26.

Zwickl, Immunogenicity of Biosynthetic Human LysPro Insulin Compared to Native–sequence Human and Purified Porcine Insulins in Rhesus Monkeys Immunized Over a 6–Week Period; *Arzneum–Forsch/Drug Res.* 45, 524–530 (1995).

Johnson, et al, Improved Technique Utilizing Nonfat Dry Milk for Analysis of Proteins and Nucleic Acids Transferred to Nitrocellulose, *Gene Anal Techn* 1:3–8.

*Primary Examiner*—Jon P. Weber
*Attorney, Agent, or Firm*—James P. Leeds; Ronald S. Maciak; David E. Boone

[57] ABSTRACT

A method for potentiating the activity of tissue plasminogen activator proteins by adding certain amounts of beta-lactoglobulin A is claimed. In particular, the invention includes an enhanced solid-phase immunoassay for measuring tissue plasminogen activator (nt-PA) activity in a mammalian serum sample with sufficient sensitivity to detect neutralizing activity in samples containing μg/ml levels of total nt-PA antibody. Neutralizing activity can be easily detected in serum dilutions containing as little as 0.038 to 0.48 μg of total nt-PA antibody in a 20 μl sample. The assay has a sensitivity of 1 pM of nt-PA (67 pg/ml) in 5 hr.

4 Claims, No Drawings

METHOD FOR POTENTIATING TISSUE PLASMINOGEN ACTIVATOR WITH β-LACTOGLOBULIN

TECHNICAL FIELD OF INVENTION

The invention pertains to the general field of human medicine and biomedical research and particularily relates tissue plasminogen activators.

BACKGROUND

The formation of potentially neutralizing antibodies in patients treated with therapeutic macromolecules, e.g. heterologous recombinant proteins, continues to be a concern to clinicians. Not only is the ability of the antibody to neutralize the therapeutic effectiveness of the protein a concern but, equally important is the possibility that these antibodies may interfere with the activity of the patient's endogenously produced protein.

Unfortunately, the extent of direct inhibitory activity in a given antiserum cannot be predicted from titer alone. For example, although antibodies that are capable of inhibiting the functions of biomolecules have been usefully employed as research and clinical tools for many years, antibody preparations that possess neutralizing activity are exceptional, typically being found only after screening many samples of high-titer antisera or hybridoma supernatants. With respect to antibody responses obtained clinically against human proteins, several factors further complicate the ability to predict whether neutralizing antibodies might be produced at levels sufficient to alter the clinical response. These include the general tendencies of these responses to be of low titer, to plateau or decrease under continued therapy, and to often involve low affinity antibodies. Presently, it is necessary to first isolate and concentrate serum samples potentially containing low levels of direct inhibitory activity that is unrelated to pharmacokinetics, metabolism, etc. to determine the existence and extent of antibody reactive with a therapeutic biomolecule. In particular, the methods of the present invention are useful for determining the presence of very low levels of antibodies or other inhibitors of t-PA activity by first potentiating the t-PA activity used in the assay. In this embodiment, the invention provides an assay means that avoides the need to first isolate and concentrate the sample.

SUMMARY OF THE INVENTION

A method for increasing the enzymatic activity of a tissue plasminogen activator protein which comprises adding from 5 to 50 µg/ml of beta lactoglobulin A to a composition containing the tissue plasminogen activator protein is claimed. Also, a sensitive method for determining tissue plasminogen activator activity in a mammalian blood sample of the type wherein a purified anti-tissue plasminogen activator capture antibody is adsorbed to an assay surface by contacting a coating solution containing the capture antibody with the assay surface and wherein the tissue plasminogen activator activity is quantitated by adding known amounts of glu-plasminogen and a chromogenic substrate, the improvement comprising, adding beta-lactoglobulin A to the coating solution at a final concentration of about 5 to 50 µg/ml, is claimed.

DETAILED DESCRIPTION OF THE INVENTION

The present invention provides a method for enhancing the enzymatic activity of tissue plasminogen activator (t-PA) proteins and is useful for enhancing the sensitivity of solid-phase immunoassays for measuring t-PA activity in blood samples. The invention is based on the unexpected observation that adding purified beta lactoglobulin A (b-LG) to the coating solution of a t-PA immunoassay increased the enzymatic activity of t-PA.

Native tissue plasminogen activator (nt-PA) is a 65–72 kD glycoprotein that plays an active role in tissue repair and remodeling by initiating fibrinolytic mechanisms in response to tissue injury and other physiologic stimuli (Collen, 1980; Takada and Takada, 1993). Its potent fibrinolytic activity has earned it a place in the pharmacopoeia as an emergency treatment for myocardial infarction (Bang et al., 1989; Grines, 1992). Because nt-PA has enzymatic activity associated with its therapeutic use, and is known to be immunogenic in rhesus monkeys, treatment of monkeys with nt-PA or mt-PA 6 (a modified nt-PA consisting of the serine protease and 2nd kringle domains) provided a useful general model for investigating the potential of clinically relevant levels of antibodies to directly inhibit the activity of therapeutic enzymes.

In recent years, a growing body or nt-PA variants and analogs have been disclosed. The following list of U.S. Patents either disclose or claim a variety of nt-PA derivatives or analogs and is provided for illustrative purposes only and is not meant to limit the present invention in any way. 5,409,699; 5,385,732; 5,366,886; 5,338,546; 5,314,818; 5,244,675; 5,100,666; 5,094,953; 5,047,241; 5,037,752; 5,002,887; 4,963,357; and 4,600,580.

The addition of beta-lactoglobulin A to the coating buffer increases the enzymatic activity of the nt-PA that is used to charge the assay surface. Consequently, it is possible to detect and quantitate lower levels of nt-PA while maintaining the strength of the reporting signal. In so doing, the assay is made more sensitive which also facilitates detection of substances that inhibit the enzymatic activity of nt-PA. Such inhibitory substances include, but are not limited to, neutralizing antibodies. It is exected that, in this embodiment, the invention would also demonstrate superior sensitivity for detecting and quantitating other substances that inhibit t-PA activity, such as plasminogen activator inhibitors that are normally found in mammalian blood. The sensitivity of the assay was found to be similar to enhanced solution-phase assays (Verheijen et al., 1982a), more than an order of magnitude greater than a comparable solid-phase activity assay (Mahmoud and Gaffney, 1985), and more than two orders of magnitude greater than the solid-phase activity assay reported by Buessecker et al., 1993.

By way of illustration, the following examples are provided to help describe how to make and practice the various embodiments of the invention. These example are in no way meant to limit the scope of the invention.

EXAMPLE 1

Materials

Recombinant human tissue plasminogen activator (nt-PA; Alteplase®) was purchased from Genentech Inc,, South San Francisco, Calif. Recombinant modified human tissue plasminogen activator (mt-PA 6), a 40 kD fragment of nt-PA containing kringle 2 and the serine protease (catalytic) domain was prepared as described in Burck et al. (1990) Journal Biol. Chem., 265(9), pages 5170–5177. Human glu-plasminogen was purchased from American Diagnostica Inc. (Greenwich, Conn.). Chromogenic substrate S-2251 was purchased from Chromogenix AB (Mölndal, Sweden).

t-PA stimulator (fibrin fragments) was purchased from Kabi Diagnostica (Mölndal, Sweden). Purified b-lactoglobulin A, poly-L-lysine, Tween 20, Tween 80, and Freund's complete (containing *Mycobacterium tuberculosis* strain H37-Ra) and incomplete adjuvants were purchased from Sigma Chemical Co. (St. Louis, Mo.). Goat-anti-monkey IgG (H+L chain specific), goat-anti-rabbit IgG (H+L chain specific), purified monkey and rabbit IgGs, and HRP-labeled goat-anti-monkey and goat anti-rabbit IgGs were purchased from Cappel Laboratories (Durham, N.C.). Two component tetramethylbenzidine (TMB) substrate solution was purchased from Kirkegaard & Perry Laboratories (Gaithersburg, Md.). Carnation non-fat dry milk was from a local grocer. All other chemicals were ACS grade or better. MaxiSorp® 96-well flat bottom plates (Nunc, Inc., Naperville, Ill.) were used for both ELISA and nt-PA activity assays.

EXAMPLE 2

Animals

Young adult New Zealand White rabbits (Hazelton Research Animals, Denver, Pa.) were housed individually. Weighed portions of Purina Certified Laboratory Rabbit Chow HF5325 were provided daily and water was provided ad libitum. Young adult rhesus monkeys were obtained from Charles River Laboratories (Wilmington, Mass.) and housed individually. Purina Certified Laboratory Primate Chow 5048 was provided twice daily, according to body weight. To provide a fresh source of vitamin C, the diet was supplemented daily with an orange. Water was provided ad libitum. Animal husbandry and treatment procedures were conducted in accordance with approved animal use protocols.

EXAMPLE 3

Generation of tPA Antisera

Three rabbits were immunized with nt-PA to obtain anti-nt-PA IgG to serve as the capture antibody reagent in the nt-PA activity assay and four monkeys were immunized with nt-PA or mt-PA 6 to serve as a source of neutralizing antisera. Dosage forms of the immunogen consisted of emulsified mixtures containing the antigen dissolved in saline, Freund's adjuvant (Sigma Chemical Co., St. Louis, Mo.), and 2% Tween 80 (Sigma) in saline in final ratios of 1:1:2. Animals were injected weekly for 6 weeks with escalating doses of antigen starting with an initial dose of 10 µg/animal and ending with 100 µg/animal. Complete Freund's adjuvant was used to prepare the initial dose and incomplete adjuvant was used to prepare all subsequent doses. Mixtures were emulsified using a Mini-Beadbeater (Biospec Products, Bartlesville, Okla.) and a divided dose of 0.5 ml was injected intramuscularly into two sites in each animal. Approximately two weeks after the final injection, blood was drawn and the serum was separated and stored at −75° C. Maintenance doses containing 100 µg nt-PA were periodically injected into rabbits and an additional two bleedings were made.

EXAMPLE 4

Purification of Rabbit anti-t-PA IgG

Rabbit antisera were titrated against nt-PA in a standard ELISA assay. Since all sera contained high antibody titers, they were pooled prior to isolation of the IgG fraction. IgG was isolated from 300 ml of pooled antiserum by precipitating it twice in 50% saturated ammonium sulfate followed by passing it through a DEAE-cellulose column that was equilibrated and subsequently eluted with 0.0175M sodium phosphate buffer, pH 6.9 (Fahey and Terry, 1978). The eluate was concentrated to 100 ml (final protein concentration= 16.5 mg/ml) on a YM-30 ultrafiltration membrane (Amicon, Beverly, Mass.). In order to obtain an IgG fraction that did not bind to the catalytic domain of nt-PA, affinity chromatography was used to separate the IgG into two fractions that either a) bound or b) remained unbound to an mt-PA 6 affinity column.

Briefly, mt-PA 6 was coupled to 20 ml of Actigel-ALD Superflow beads (Sterogene Bioseparations, Arcadia, Calif.) according to the manufacturer's instructions. An HR16/5 column (Pharmacia LKB Biotechnology, Piscataway, N.J.) was packed with the mt-PA 6-conjugated beads. Chromatography was conducted on an FPLC unit (Pharmacia LKB) at room temperature. Potassium phosphate-buffered saline, pH 7.0, containing 0.01% thimerosal was used to load 1.0 ml/run of IgG solution and to elute the unbound fraction. Bound fractions were eluted with 0.5M ammonium acetate, pH 3.0. Bound and unbound fractions from all runs were pooled separately, equilibrated in potassium phosphate buffer containing thimerosal, concentrated by ultrafiltration on YM-30 membranes and filtered through 0.22 µm cellulose acetate filter units. Protein concentrations were determined by 280 nm absorbance, then the solutions were aliquotted and stored at −75° C.

EXAMPLE 5

Noise-Reduction ELISA Assay for tPA Antibodies

Serum samples were prepared from blood samples drawn from the monkeys and rabbits. The serum samples were assayed for antibody against nt-PA or mt-PA 6 using the following methods that were optimized to run on a Biomek 1000 Laboratory Workstation (Beckman Instruments, Inc., Fullerton, Calif.).

A. Coating Solutions

Coating buffer was 0.1M sodium bicarbonate, pH 9.6, containing 0.02% sodium azide. b-LG was added to a final concentration of 20 µg/ml in order to reduce non-specific binding of immunoglobulin. This solution was used to prepare coating solutions containing 50 µg/ml of nt-PA, mt-PA 6, or goat anti-monkey (or rabbit) IgG.

B. Rinse Solutions

To rinse the plates between various steps, 0.02M potassium phosphate buffered saline, pH 7.3 (KPBS), containing 0.01% porcine gelatin and 0.05% Tween 20, was used. Plates were rinsed using 3 fill/aspirate cycles per rinse.

C. Blocking and Sample Dilution Buffer

Noise-reduction buffer (NR-ELISA buffer), consisted of 50 mM Hepes, 0.4M sodium chloride, 3.8 mM disodium EDTA, 0.5% Tween 20, and 0.5% (wt/vol) milk protein that had been dialyzed against EDTA to remove calcium. The formulation of this buffer is similar to one reported by Graves (1988) with the exceptions that a lower concentration of EDTA was used and milk protein was added. To prepare 3 liters of buffer, 15 g of powdered milk was added to 300 ml of water and stirred under low heat. The solution was dialyzed against two changes of 0.01M tetrasodium EDTA, followed by two changes of water using dialysis tubing with a 14,000 molecular weight cutoff (Spectrum Medical industries, Inc., Los Angeles, Calif.). To approximately 2300 ml of water, 35.7 g of Hepes free acid, 70.1 g of sodium chloride, and 3.8 g of disodium EDTA were added. The pH was adjusted to 7.0 with 1N sodium hydroxide, the entire volume of dialyzed milk solution was added, and the volume was adjusted to 3 L with water.

D. Enzyme Conjugate

Peroxidase (HRP)-labeled goat anti-monkey (or rabbit) IgG was used to develop the ELISA. To remove the small amount of crossreactivity to IgM in the anti-monkey conjugate, it was passed over a monkey IgM affinity column. Conjugates were diluted in 0.02M KPBS containing 0.1% porcine gelatin. The final dilution of each conjugate was determined empirically.

E. Substrate and Stopping Solutions

Commercially available TMB substrate solution was used. To stop the reaction, an equal volume of 1M phosphoric acid was added to each well.

F. Procedure

All incubations were carried out at room temperature; plates were sealed with acetate plate sealers during each incubation step up to the time substrate was added. Wells were coated with 100 µl/well of the various coating solutions, according to the type of assay. After coating, plates were rinsed and blocked with 150 µl/well of blocking buffer for 30 min. Plates were rinsed and 100 µl/well of serially diluted reference standards and samples were added, in duplicate, to appropriate wells. Reference IgG standards were placed in wells coated with goat anti-monkey (or rabbit) IgG. To serve as a blank for the reference curve, NR-ELISA buffer alone was placed in two of the coated wells. Two-fold serial dilutions of each serum sample were assayed in wells coated with nt-PA or mt-PA 6. After a 60 min incubation, plates were rinsed and 100 µl/well of HRP-goat anti-monkey (or rabbit) IgG was added to each well. The plates were incubated with the HRP-conjugate for 60 min, rinsed, then filled with 100 µl/well of substrate solution. Absorbances of the wells that contained the highest IgG reference standard were monitored at 660 nm. When the readings from those wells reached a mean of 0.90 absorbance units, the reaction was stopped in the entire plate by adding 100 µl/well of stopping solution. Plates were shaken on a Mini-Orbital Shaker (Bellco Glass, Inc., Vineland, N.J.) then read on an MR5000 microplate reader (Dynatech Laboratories, Inc., Alexandria, Va.) at a test wavelength of 450 nm and a reference wavelength of 590 nm using Titercalc 2.1 software (HP-Genenchem, Palo Alto, Calif.).

EXAMPLE 6

Solid-Phase Assay for t-PA Activity

The assay was based on a procedure described by Mahmoud and Gaffney (1985). Exceptions included the use of assay buffers and incubation conditions chosen to make the assay easily amenable to conversion into a semi-automated ELISA assay for nt-PA antigen and those modifications that were made to investigate factors affecting assay sensitivity. Plates were coated overnight at 5° C. with 150 µl/well of ELISA coating buffer containing capture antibody with or without b-LG. After coating, all remaining steps were conducted at approximately 22° C. Plates were rinsed with one cycle of ELISA rinse buffer then blocked with 300 µl/well of NR-ELISA buffer for 30 min. After rinsing, wells were filled with 180 µl of NR-ELISA buffer and charged with nt-PA by adding 20 µl of nt-PA solution, diluted to various concentrations in NR-ELISA buffer, and incubating for 60 min. When assaying for neutralizing activity in monkey antisera, plates were rinsed and filled with 180 µl/well of NR-ELISA buffer and 20 µl of undiluted or diluted antiserum. Plates were shaken, covered, and incubated for 60 min. To develop the assay, plates were rinsed and 110 µl of 0.75 mM substrate S-2251 and 40 µl of 0.1 mg/ml glu-plasminogen were added. Plates were shaken, covered, and monitored at various time points for absorbance at 405 nm (using a reference wavelength of 490 nm) with an MR5000 microplate reader and BioLinx 2.1 software (Dynatech). Comparison of the kinetics on this assay in the absence and presence of b-LG are shown below.

| Incubation Time (minutes) | Absorbance at 405 nm | |
|---|---|---|
| | (without b-LG) | (with b-LG) |
| 12 | 0.020 | 0.026 |
| 30 | 0.023 | 0.077 |
| 90 | 0.093 | 0.460 |
| 120 | 0.171 | 0.673 |
| 180 | 0.329 | 0.917 |
| 210 | 0.409 | 1.003 |
| 240 | 0.498 | 1.063 |

We claim:

1. A method for increasing the enzymatic activity of a mammalian tissue plasminogen activator protein which comprises adding from 5 to 50 µg/mL of beta lactoglobulin A to a composition containing the mammalian tissue plasminogen activator protein.

2. The method of claim 1 wherein the tissue plasminogen activator protein is selected from the group consisting of native tissue plasminogen activator and modified tissue plasminogen activator 6 (mt-PA 6).

3. The method of claim 1 wherein said tissue plasminogen activator protein is native tissue plasminogen activator.

4. The method of claim 1 wherein said tissue plasminogen activator protein is mt-PA 6.

* * * * *